United States Patent [19]

Benkó et al.

[11] Patent Number: 4,746,678

[45] Date of Patent: May 24, 1988

[54] PHENANTHRENE DERIVATIVES

[75] Inventors: Pál Benkó, Budapest; Tibor Zsolnai, Debrecen; Márta Kininczky; László Pallos, both of Budapest; Irén Zsolnai née Csillag, Debrecen; Péter Tétényi; Jenö Bernáth, both of Budapest, all of Hungary

[73] Assignee: EGIS Gyoryszergyar, Budapest, Hungary

[21] Appl. No.: 870,402

[22] Filed: Jun. 4, 1986

[30] Foreign Application Priority Data

Jun. 4, 1985 [HU] Hungary .............................. 2194/85

[51] Int. Cl.[4] .............................................. A61K 31/15
[52] U.S. Cl. ..................... 514/640; 514/477; 514/510; 514/512; 514/522; 558/248; 558/262; 558/416; 564/254; 564/255
[58] Field of Search ............... 564/254, 255; 558/248, 558/262, 416; 514/477, 510, 512, 641, 522, 640

[56] References Cited

U.S. PATENT DOCUMENTS 3,547,621 12/1970 Neighbors et al. ................. 564/254

FOREIGN PATENT DOCUMENTS 719039 2/1969 Belgium .............................. 564/254

OTHER PUBLICATIONS

Degering, Ed. F. *An Outline of Organic Nitrogen Compounds* (1950), at p. 181, Publ. Univ. Lithoprinters, Ypsilanti, Mich.

Primary Examiner—James H. Reamer
Attorney, Agent, or Firm—Keil & Weinkauf

[57] ABSTRACT

The invention relates to new phenanthrene derivatives wherein R stand for $C_{1-10}$ alkylamino; $C_{1-10}$ alkylthio; $C_{1-5}$ alkoxy; or phenyl or phenylamino, the two latter groups being optionally substituted on the phenyl ring by one or more identical or different $C_{1-4}$ alkyl, $C_{1-4}$ alkoxy, nitro, amino, cyano and/or halogen substituent(s).

The compounds of the present invention possess valuable fungicidal properties and may be used in agriculture, horticulture and therapy as active ingredient of fungicidal or antifungal compositions.

The compounds of the general Formula I

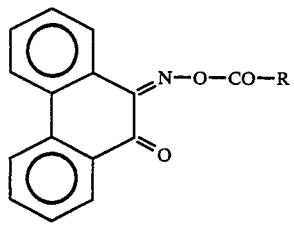

(I)

may be prepared by acylating 9,10-phenanthrene-dione-9-oxime or an alkali or alkali earth metal salt thereof.

12 Claims, No Drawings

PHENANTHRENE DERIVATIVES

This invention relates to new phenanthrene derivatives, a process for the preparation thereof, fungicidal compositions for use in agriculture, horticulture and human and veterinary therapy containing the same.

According to an aspect of the present invention there are provided new phenanthrene derivatives of the Formula I

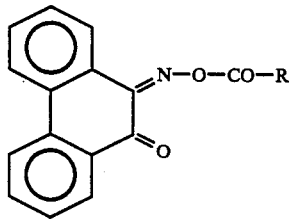

(I)

wherein, R stands for $C_{1-10}$ alkylamino; $C_{1-10}$ alkylthio; $C_{1-5}$ alkoxy; or phenyl or phenylamino, the two latter groups being optionally substituted on the phenyl ring by one or more identical or different $C_{1-4}$ alkyl, $C_{1-4}$ alkoxy, nitro, amino, cyano and/or halogen substituent(s).

The term "alkyl" used throughout the specification relates to straight or branched chained alkyl groups (e.g. methyl, ethyl, n-propyl, isopropyl, n-butyl, iso-amyl). The term "alkoxy" relates to straight or branched chained alkoxy groups (e.g. methoxy, ethoxy, propoxy or isopropoxy). The term "halogen" encompasses the fluorine, chlorine, bromine and iodine atoms.

R as $C_{1-10}$ alkylamino stands preferably for methylamino, ethylamino, n-propylamino, or n-butylamino.

R as $C_{1-10}$ alkylthio represents preferably methylthio, ethylthio, n-propylthio, n-butylthio or n-octylthio.

R as $C_{1-5}$ alkoxy stands preferably for methoxy or ethoxy.

R as optionally substituted phenyl stands preferably for phenyl optionally substituted by one or two identical or different methyl, ethyl, methoxy, ethoxy, cyano, chlorine and/or bromine substituents.

R as optionally substituted phenylamino represents preferably phenylamino optionally bearing one or two identical or different methyl, ethyl, methoxy, ethoxy, cyano, chlorine and/or bromine substituents.

Particularly preferred representatives of the compounds of the Formula I are the following derivatives: 9,10-phenanthrene-dione-9-(methylaminocarbonyl)-oxime and 9,10-phenanthrene-dione-9-(n-butylaminocarbonyl)-oxime.

The new compounds of the general Formula I exhibit fungicidal effect. According to our extended tests and new compounds of the present invention are active against all human pathogenic filamentous dermatophytons (Trichophytones, Epidermophytons, Microsporons) and a large number of plant pathogenic fungi strains (Fusarium, Helminthosporium, Schlerotonia, Nigrospora etc.). The compounds of the Formula I may be successfully applied onto the leaves as well as in water and soil.

The compounds of the Formula I show a wide activity spectrum [e.g. similar to N-(trichloromethylthio)-phthalimide and bis(dimethyl-thiocarbamoyl)-disulfide]. The intensity of the effect is in vitro approximately of the same order of magnitude as that of the above commercial products, however when tested in vivo, the compounds of the Formula I are superior to the known agents.

Preferred representatives of the compounds of the Formula I when used in the form of a spray having an active ingredient content of 0.05-0.1% provide in vivo excellent and safe protection against powdery mildew of cereals, cucumber, parsley and beet. The intensity of effect is of the same order of magnitude as that of benomyl [methyl-1-(n-butylcarbamoyl)-2-benzimidazole-carbamate]. A spray comprising 0.05% of a compound of the Formula I is also effective against Uromyces apperdiculatus (bean rust).

Against Uromyces apperdiculatus the compounds of the Formula I are approximately as active as the commercial product "dithane" (active ingredient: manganese+zinc ethylene-bis-dithiocarbamate).

The compounds of the Formula I are not phytotoxic towards cultivated plants in the concentrations used.

The fungicidal activity of the compounds of the Formula I is determined by the following in vitro method:

A 0.5% alcoholic solution of the test-compound is prepared and 1.0, 0.4, 0.2 and 0.1 ml amounts of the solution, respectively, are uniformly admixed with 50 ml of a Sabouraud-type nutrient medium. The nutrient media are allowed to solidity whereupon the surface is inoculated with a spore suspension of the test Fungi strain.

The following fungi and bacterial strains are used for the test:

| | |
|---|---|
| | Alternaria tenuis |
| Trichophyton gypseum | Cladosporium herbarum |
| Trichophyton simii | Stemphylium radicinum |
| Epidermophyton longifusum | Cercospora beticola |
| Microsporon gypseum | Verticillium alboatrum |
| Fusarium graminearum | Rhizoctonia solani |
| Fusarium culmorum | Ascochyta pisi |
| Helminthosporium sativum | Corynebacterium |
| Helminthosporium papaveris | michiganense |
| Nigrospora oryzae | Xanthomonas vesicatoria |
| Sclerotinia schlerotiorum | Erwinia carotovora |
| Monilia laxa | Pseudomonas syringae |
| Botrytis cinerea arium | Micrococcus luteus |
| Colletotrichum atrament | Agrobacterium tumefaciens |

The concentration of the active ingredient in the Petri-dishes amounts to 100, 40, 20 and 10 μg/ml, respectively. The activity is determined after 5 days of incubation at a temperature of 28° C.

It has been found that the most active representatives of the compounds of the Formula I (the compounds prepared according to Examples 1, 4, 5, 7 and 8) exhibit in vitro fungistatic effect against most test fungi strains (particularly on Trichophyton, Monilia and Helminthosporum) already in a concentration of 10–20 μg/ml. On the other hand, known commercial fungicides, as N-(trichloromethylthio)-phthalimide and bis-(dimethylthiocarbamoyl)-disulfide, exert the same activity only in a higher concentration of 40–100 μg/ml.

In vivo tests are carried out against cereals powdery mildew.

In vivo activity is tested against wheat powdery mildew in a phytobox of the Conviron type, at 20° C., a relative humidity of 90% and a light intensity of 9000 lux. As host plant the elite propagating seed grain material of officially qualified "MV-4" wheat species is used. Wheat plants are cultivated in 6 days' periods, in cultivating dishes (diameter 11 cm) containing a 1:1 mixture of sand and perlite. Each dish contains 160 plants; at the beginning of the treatment the plants were 5–6 cm high. High dispersity grade aqueous suspensions or acetonic solutions of the test compound are prepared and 8 ml of each suspension or solution, respectively, are applied onto the plants by means of a spraying apparatus operated by gaseous nitrogen. Inoculation is carried out 24 days after the fungicidal treatment. The test units are placed in three replicates and in random block arrangement in the phytotron. The rate of infectedness is determined on the 8th day after inoculation. Numerical evaluation is accomplished on the basis of the method described by Hinfner and Papp by observing separately 50–60 plants.

The infectedness of the untreated controls is very high; most plants become infected and approximately 30–40% of the surface of the plants is effected by the infection.

Commercially available fungicides [e.g. 1-butyl-carbamoyl-benzimidazole-2-methyl-carbamate and 6-(1-methyl-heptyl-2,4-dinitro-phenyl-crotonate)] show under identical test conditions lower activity than the most efficient representatives of the novel compounds (products of Examples 7 and 8).

The results are expressed as $ED_{50}$ and $ED_{90}$ values of the test compounds being calculated from the co-relation of effect and concentration by means of mathematical-biometrical methods. The $ED_{50}$ and $ED_{90}$ values, respectively, are those active ingredient concentrations of the spray (in ppm) which are capable of decreasing the powdery mildew infectedness of the test plants by 50% and 90%, respectively (related to the untreated control).

The results are summarized in Table I.

TABLE I

| Test compound | $ED_{50}$ (ppm) | $ED_{90}$ (ppm) |
| --- | --- | --- |
| Example 8 | 357 | 1336 |
| Example 7 | 346 | 1101 |
| Reference compound[x] | 410 | 1455 |

[x] = Benomyl = 1-n-butyl-carbamoyl-benzimidazole-2-methyl-carbamate

A further test is carried out on "pinto" bean species against bean rust (Uromyces apperdiculatus). Into each cultivating dish three seeds are sown in a 1:1:0.035 mixture of sand, perlite and super compost. Two-leave staged bean plants subjected to 7–9 days' glass house pre-cultivation are treated with the test compound and the treated plants are inoculated. The concentration of the spore suspension amounts to 0.1 g/10 ml and 2.5 ml of spore suspension are used for each cultivating dish. After inoculation the plants are incubated at 20° C. under a relative moisture content of 100% for 48 hours. The symptoms manifest themselves 7–8 days after infection. Three replicates are used; untreated control treatment is also carried out and the commercial product "Dithane M 45" serves as reference.

The results show that Dithane M-45 inhibits by 70–80% bean rust infection when applied as a spray at a concentration of 500 ppm. Compounds of Examples 7 and 8 of the present invention achieve 100% inhibition under identical conditions.

According to a further aspect of the present invention there are provided fungicidal compositions comprising in an effective amount at least one compound of the Formula I (wherein R is as stated above) in admixture with suitable solid or liquid carriers and optionally further additives.

The active ingredients of the Formula I may be formulated into fungicidal compositions generally used in agriculture and horticulture for plant protecting purposes, e.g. powder formulations, wettable powders, sprays, oily sprays, aerosols, emulsifiable, concentrates, granules, micronized granular compositions etc.

The fungicidal compositions of the present invention comprise usual and conventional solid carriers or diluents. For this purpose preferably the following materials may be used: minerals in powdered or granular form (e.g. talc, bentonite, montmorillonite, China clay, kaolin, highly dispersed silicagel, diatomaceous earth, mica, apatite, vermiculite, gypsum, limestone, pyrophyllite, sericite, pumice, sulfur, activated charcoal, slacked lime, perlite etc.), powders of vegetable origin (e.g. soya wheat, wood, nutshell, sawdust, bran, cortex, bark, extraction residue of plants, starch, crystalline cellulose); powdered polymeric materials (e.g. PVC, dammar resin, ketone resin etc); fibrous materials (e.g. paper, corrugated board, waste cloth); chemical fertilizers (e.g. ammonium sulfate, ammonium phosphate, ammonium nitrate, urea, ammonium chloride etc.); or aluminous earth or wax.

The compositions may also comprise conventional and usual liquid diluents, e.g. alcohols (such as methanol, ethanol, isopropanol, ethylene glycol, polyethylene glycol, benzyl alcohol); aromatic hydrocarbons (e.g. benzene, xylene, toluene, methyl naphthalene); aliphatic hydrocarbons (e.g. kerozene, hexane); chlorinated hydrocarbons (e.g. chloroform, carbon tetrachloride, chlorobenzene, trichloro ethylene, dichloromethane etc.); ethers (e.g. diethyl ether, diisopropyl ether, dioxane, tetrahydrofurane, ethylene glycol ethyl ether); ketones (e.g. acetone, methyl ethyl ketone, cyclohexanone); esters (e.g. ethyl acetate, ethylene glycol acetate); acid amides (e.g. N,N-dimethyl formamide); nitriles (e.g. acetonitrile) or sulfoxides (e.g. dimethyl sulfoxide).

The fungicidal compositions of the present invention may comprise further additives, too, e.g. binding and/or dispersing agents (such as gelatine, caseine, sodium alginate, carboxy methyl cellulose, starch, lignosulfonate, bentonite, polyoxy propylene glycol ether, polyvinyl alcohol, paraffine), stabilizers (e.g. isopropyl phosphate, tricresyl phosphate, tall oil, epoxidized oil, surfactants, fatty acids, fatty acid ethers); emulsifiers (e.g. alkyl sulfonate, polyoxy-ethylene-alkyl sulfonate, alkyl aryl sulfonate, polyethylene glycol alkyl ether, or polyoxy ethylene alkyl aryl ether etc.), wetting agents (e.g. dodecyl benzene sulfonate, lauryl sulfonate, alkyl naphthalene sulfonate salts).

The fungicidal compositions of the present invention may, in addition to the phenanthrene derivatives of the Formula I, comprise one or more further biologically active agents, e.g. propagating material and/or other fungicides, such as aluminium-tris(ethyl phosphonate), 2-amino-butane, 4,6-dichloro-2-(2-chloroanilino)-1,3,5-triazine, 2-iodo-benzanilide, methyl-1-(butylcarbamoyl)-2-benzimidazole-carbamate, 1,4-benzoquinone-1-benzoyl-hydrazone-4-oxime, 2-sec. butyl-4,6-dinitro-phenyl-3-methyl-crotonate, $\beta$-[(1,1'-diphenyl)-4-yloxy]-$\alpha$-(1,1-dimethylethyl)-1H-1,2,4-triazole-1-ethanol, 1,2,3,6-tetrahydro-N-(1,1,2,2-tetrachloroethylthio)-phthalimide, 1,2,3,6-tetrahydro-N-(trichloromethylthio)-phthalimide, 2-(methoxycarbonylamino)-benzimidazole, 5,6-dihydro-2-methyl-1,4-oxatiine-3-carboxanilide, polyoxine, validamycin, streptomycin, dodecyl guanidinyl acetate, 1-(4-chlorphenoxy)-1-(imidazole-1-yl)-3,3-dimethyl-butanone, tetrahydro-3,5-dimethyl-1,3,5-thiadiazine-2-thione, N-dichloro-fluoro-methylthio-N',N'-dimethyl-N-phenylsulfamide, 2,3-dichloro-1,4-naphthoquinone, 5-butyl-2-dimethylamino-4-hydroxy-6-methyl-pyrimidine, 2- or 4-(1-methyl-heptyl)-4,6- (or 2,6)-dinitro-phenyl-crotonate, 2,3-dicyano-1,4-dithio-antraquinone, 5-butyl-2-ethylamino-4-hydroxy-6-methyl-pyrimidine, 2-methyl-furane-3-carboxanilide, N-(trichloromethylthio)-phthalimide, 2-heptadecyl-2-imidazolinium acetate, 7-bromo-5-chloro-quinoline-8-yl acrylate, 8-hidroxy quinoline and salts thereof, 1-(β-allyloxy-2,4-dichlorophenyl-ethyl)-imidazole, N-(2-methoxyacetyl)-N-(2,6-xylyl)-DL-alanine methyl ester, 2,4,5-trimethyl-N-phenyl-3-furane-carboxylic acid amide, 2-(4-thiazolyl)-1H-benzimidazole, 1,2-bis-(3-ethoxycarbonyl)-2-thioureido)-benzene, 1-(4-chloro-phenoxy)-3,3-dimethyl-1-(1,2,4-triazole-1-yl)-butanol etc.

The compositions according to the present invention may also comprise, in addition to the active ingredient of the Formula I, one or more insecticidal agents, e.g. 2-methoxy-4H-1,3,2-benzodioxa-phosphorine-2-sulfide, (5-benzyl-3-hydroxy-methyl-furane)-d-trans-chrysanthemate, 3-phenoxybenzyl-chrysanthemate, O,O-diethyl-1-(2,4-dichlorophenyl)-2-chlorovinyl-phosphate, 2,2-dimethyl-3-(2,2-dichlorovinyl)-cyclopropane carboxylic acid α-cyano-2-phenoxy-benzyl ester, O,O-diethyl-O-(2-isopropyl-4-methyl-pyrimidinyl)-thiophosphate, 2,3-dihydro-2,2-dimethyl-7-benzofuranyl-N-methyl-carbamate etc.

In the above compositions the pesticidal activity of the individual components is not decreased and for this reason the said combinations enable the simultaneous combating of two or more pests (fungi, insects). The compositions of the present invention may also comprise further agents used in agriculture and horticulture, e.g. insecticides active against filamentous insects and moth (e.g. succinic acid 2,2-dimethyl hydrazide, 2-chloroethyl-trimethyl ammonium chloride, 2-chloroethyl-phosphonic acid, 1,1-dimethyl-piperidinium-chloride). Fertilizers may also be added to the compositions of the present invention.

The active ingredient content of the compositions of the present invention may vary between wide ranges and may be generally e.g. 0.001-95.0% by weight, preferably 5-80% by weight. The general dose of the active ingredient may be preferably 100-1000 g/ha and the concentration of the ready-for-use compositions may be about 0.01-0.1% by weight. The active ingredient may also be formulated in the form of concentrates (20-60%) which are easy to handle, transport and are highly suitable for storage. The said intervals are, however, but of informative character; the actual dose and concentration depends on various factors (e.g. type of the formulation, mode and site of application, seriousness of the fungal disease, the crop to be treated etc.) and may be also below or above the said values.

The fungicidal compositions of the present invention may be prepared by known methods of pesticidal industry.

According to a further feature of the present invention there are provided pharmaceutical compositions having antifungal effect comprising as active ingredient at least one compound of the Formula I in admixture with suitable inert solid or liquid pharmaceutical carriers.

The said pharmaceutical compositions may be prepared by methods of pharmaceutical industry known per se.

According to a still further feature of the present invention there is provided a process for the preparation of phenanthrene derivatives of the Formula I (wherein R is as stated above) which comprises (a) for the preparation of compounds of the Formula I, wherein R stands for $C_{1-10}$ alkylamino or phenylamino optionally bearing on the phenyl ring one or more identical or different $C_{1-4}$ alkyl, $C_{1-4}$ alkoxy, nitro, amino, cyano and/or halogen substituent(s), reacting phenanthrene-9,10-dione-9-oxime of the Formula II

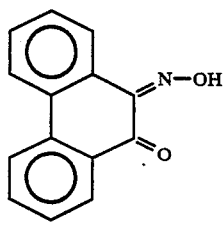

(II)

with an isocyanate of the Formula IV

$R_1$—NCO  (IV)

(a) wherein $R_1$ stands for $C_{1-10}$ alkyl or phenyl optionally substituted by one or more identical or different $C_{1-4}$ alkyl, $C_{1-4}$ alkoxy, nitro, amino, cyano and/or halogen substituent(s); or (b) for the preparation of compounds of the Formula I, wherein R stands for $C_{1-5}$ alkoxy or $C_{1-10}$ alkylthio, reacting phenanthrene-9,10-dione-9-oxime of the Formula II or an alkali or alkali earth metal salt thereof of the Formula III

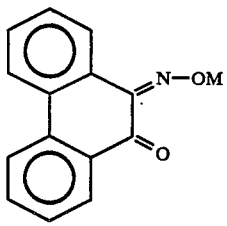

(III)

(wherein M is one equivalent of an alkali or alkali earth metal) with a compound of the Formula V

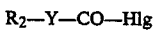

$R_2$—Y—CO—Hlg  (V)

(wherein $R_2$ stands for $C_{1-10}$ alkyl; Y represents oxygen or sulfur and Hlg is halogen); or (c) for the preparation of compounds of the Formula I, wherein R stands for phenyl optionally bearing one or more identical or different $C_{1-4}$ alkyl, $C_{1-4}$ alkoxy, nitro, amino, cyano and/or halogen substituent(s), reacting phenanthrene-dione-9-oxime of the Formula II or an alkali metal or alkali earth metal salt of the Formula III thereof (wherein M is as stated above) with a compound of the general Formula VI

$R_3$—CO—X  (VI)

(wherein $R_3$ stands for phenyl optionally bearing one or more identical or different $C_{1-4}$ alkyl, $C_{1-4}$ alkoxy, nitro, amino, cyano and/or halogen substituent(s) and X represents a leaving group).

According to method (a) of the process of the present invention 9,10-phenanthrene-dione-monooxime of the Formula II is reacted with an isocyanate of the Formula IV. The reaction may be carried out in an inert organic solvent. As reaction medium e.g. an aromatic hydrocarbon (e.g. benzene or xylene), an ether (e.g. tetrahydrofuran, dioxane), a halogenated solvent (e.g. chloroform, dichloroethane or carbon tetrachloride) may be used. One works advantageously under anhydrous conditions. A nucleophilic catalyst may also be added to the reaction mixture. For this purpose tertiary amines (e.g. N-ethyl-piperidine or triethyl amine) may be applied. The reaction may be accomplished at a temperature between 0° C. and 35° C., advantageously at ambient temperature. The reaction takes place within a period of about 0.5 to 6 hours; at room-temperature the reaction time is about 1-3 hours.

According to method (b) it is preferred to use starting materials of the Formula V, wherein Hlg is chlorine. Instead of 9,10-phenanthrene-dione-oxime of the Formula II an alkali (e.g. sodium or potassium) or alkali earth metal (e.g. calcium or magnesium) salt of the Formula III thereof may also be used. It is preferred to apply the sodium salt. The reaction may be accomplished in an inert organic solvent, (e.g. acetone, dioxane or dimethyl formamide). The reaction may be carried out at a temperature between 0° C. and 100° C., preferably at 10°-70° C.

According to a preferred form of carrying out method (b) 9,10-phenanthrene-dione-monooxime of the Formula II is reacted with a compound of Formula V in a dipolar aprotic solvent (e.g. acetonitrile, dimethyl formamide, dimethyl acetamide, dimethyl sulfoxide) optionally in the presence of a less polar aprotic solvent (e.g. pyridine, dioxane or benzene) for a period of 0.5-10 hours, particularly 1.5-3 hours.

According to method (c) 9,10-phenanthrene-dione-monooxime of the Formula II or an alkali (e.g. sodium or potassium) or alkali earth metal (e.g. calcium or magnesium) salt of the Formula III thereof is reacted with an acylating agent of the Formula VI. It is preferred to use the sodium salt of the Formula III. In the Formula of the acylating agents of the Formula VI, X stands preferably for halogen (e.g. chlorine or bromine), alkylsulfonyloxy (e.g. methylsulfonyloxy) or arylsulfonyloxy (e.g. phenyl-, p-methylphenyl- or p-bromophenyl-sulfonyloxy). The reaction may be carried out in an inert organic solvent. The reaction medium is selected under taking into consideration the character of the X leaving group. For this purpose apolar aprotic solvents (e.g. dioxane, benzene, chloroform, carbon tetrachloride) or protic solvents (e.g. formamide, acetic acid or ethanol) may be used. The reaction may be accomplished at a temperature between 0° C. and 120° C., preferably at 20°-50° C. The reaction time is about 0.5-10 hours, preferably 1-2 hours.

The starting materials used may be prepared by methods known from prior art, e.g. in accordance with the following publications:
9,10-phenanthrene-quinone [J. Am. Chem. Soc. 64, 2023 (1942)];
9,10-phenanthrene-quinone-9-oxime [Ber. 22, 1989 (1889)];
the sodium salt of the latter compound [J. Am. Chem. Soc. 76, 124-127 (1954)].

Further details of the present invention are to be found in the following Examples without limiting the scope of protection of the said Examples.

EXAMPLE 1

24.6 g (0.1 mole) of the sodium salt of 9,10-phenanthrene-dione-9-oxime are suspended in 100 ml of acetone, whereupon a solution of 15.4 g (0.11 mole) of benzoyl chloride and 50 ml of acetone is added under stirring. A slightly exothermic reaction takes place, sodium chloride is precipitated and within about an hour a dark brown solution is formed. The reaction having been completed, the reaction mixture is heated to boiling for 15 minutes and evaporated in vacuo. Thus 28.2 g of 9,10-phenanthrene-dione-9-benzoyl-oxime are obtained, yield, 86.2%, mp.: 148°-149° C.

Analysis for the Formula $C_{21}H_{13}NO_3$ calculated: C %=77.06; H %=3.98; N %=4.28; found: C %=77.15; H %=3.96; N %=4.32.

EXAMPLE 2

22.3 g (0.1 mole) of 9,10-phenanthrene-dione-9-oxime are dissolved in 200 ml of 1:1 mixture of dimethyl formamide and acetonitrile under stirring, whereupon 16 ml of pyridine are added. To the reaction mixture a solution of methyl chloroformate and 30 ml of acetonitrile is added dropwise under stirring. The reaction mixture is stirred first at room temperature for an hour and thereafter at boiling point for 15 minutes. The reaction mixture is cooled and poured into 700 ml of icecold water. On cooling the precipitated oily product solidifies. Thus 22.9 g of 9,10-phenanthrene-dione-9-methoxycarbonyl-oxime are obtained in the form of an orchre-yellow product. Yield 81.5%, mp.: 142°-143° C.

Analysis for the Formula $C_{16}H_{11}NO_4$ calculated: C %=68.32; H %=3.91; N %=4.98; found: C %=68.29; H %=3.90; N %=4.92.

EXAMPLES 3-6

One proceeds according to Example 2 except that the corresponding starting materials are used. The following compounds are prepared:

(3) 9,10-Phenanthrene-dione-9-(ethoxycarbonyl)-oxime

Analysis for the Formula $C_{17}H_{13}NO_4$ calculated: C %=69.15; H %=4.41; N %=4.75; found: C %=69.00; H %=4.39; N %=4.71.

(4) 9,10-Phenanthrene-dione-9-(ethylthiocarbonyl)-oxime

Analysis for the Formula $C_{17}H_{13}NO_3S$ calculated: C %=65.59; H %=4.18; N %=4.50; S %=10.29; found: C %=65.49; H %=4.13; N %=4.13; S %=10.29.

(5) 9,10-Phenanthrene-dione-9-(n-propylthiocarbonyl)-oxime

Analysis for the Formula $C_{18}H_{15}NO_3S$ calculated: C%=66.46; H%=4.61; N%=4.30; S%=9.84; found: C%=66.41; H%=4.60; N%=4.28; S%=9.92.

(6) 9,10-Phenanthrene-dione-9-(n-octylthiocarbonyl)-oxime

Analysis for the Formula $C_{23}H_{25}NO_3S$ calculated: C %=69.87; H %=6.33; N %=3.54; S %=8.10; found: C %=69.79; H %=6.30; N %=3.49; S %=8.18.

EXAMPLE 7

22.3 g (0.1 mole) of 9,10-phenanthrene-dione-9-oxime are reacted with 12 ml (0.11 mole) of n-butyl isocyanate in 100 ml of chloroform in the presence of 0.2 ml of triethyl amine for an hour. The reaction mixture is heated to boiling for half an hour and evaporated in vacuo. Thus 32 g of 9,10-phenanthrene-dione-9-(n-butyl-aminocarbonyl)-oxime are obtained in the form of a yellowish brown oil, yield 99%.

The product is purified by chromatography.

Analysis for the Formula $C_{19}H_{18}N_2O_3$ calculated: C %=70.81; H %=5.59; N %=8.69; found: C %=70.01; H %=5.51; N %=8.71.

EXAMPLES 8-10

One proceeds according to Example 7 except that the corresponding starting materials are used. Thus the following compounds are prepared:

(8) 9,10-Phenanthrene-dione-9-(methylaminocarbonyl)-oxime

Analysis for the Formula $C_{16}H_{12}N_2O_3$ calculated: C %=68.57; H %=4.29; N %=10.0; found: C %=68.40; H %=4.23; N %=9.89.

(9) 9,10-Phenanthrene-9-(4-chloro-phenyl-amino-carbonyl)-oxime

Analysis for the Formula $C_{21}H_{13}ClN_2O_3$ calculated: C %=67.02; H %=3.46; N %=7.44; Cl%=9.31; found: C %=67.08; H %=3.41; N %=7.39; Cl%=9.33.

(10) 9,10-Phenanthrene-dione-9-(3,4-dichloro-phenyl-amino-carbonyl)-oxime

Analysis for the Formula $C_{21}H_{12}Cl_2N_2O_3$ calculated: C %=61.46; H %=2.93; N %=6.82; Cl %=17.07; found: C %=60.99; H %=2.90; N %=6.73; Cl %=17.01.

EXAMPLE 11

Powder formulation 2 parts by weight of the compound according to Example 1 are thoroughly homogenized with 98 parts by weight of China clay. Thus a powder formulation having an active ingredient content of 2% is obtained.

EXAMPLE 12

Wettable powder 50 parts by weight of the compound according to Example 3, 2.5 parts by weight of dodecyl benzenesulfonate (wetting agent), 2.5 parts by weight of sodium-lignosulfonate (dispersing agent) and 45 parts by weight of diatomaceous earth are thoroughly admixed and homogenized. Thus a wettable powder having an active ingredient content of 56% is obtained. The said wettable powder gives a ready-for-use spray on diluting with water.

EXAMPLE 13

Wettable powder 90 parts by weight of the compound according to Example 6, 2.5 parts by weight of dodecyl benzene sulfonate, 2.5 parts by weight of sodium lignosulfonate and 5 parts by weight of diatomaceous earth are thoroughly admixed and homogenized. Thus a wettable powder having an active ingredient content of 90% is obtained which may be converted into a ready-for-use spray by diluting with water.

EXAMPLE 14

Powder formulation 0.2 part by weight of the compound according to Example 5, 1 part by weight of paraffin oil and 98.8% by weight of China clay are thoroughly admixed and homogenized. Thus a ready-for-use powder formulation having an active ingredient content of 0.2% is obtained.

EXAMPLE 15

Emulsion concentrate 20 parts by weight of the compound according to Example 8, 30 parts by weight of dimethyl sulfoxide, 40 parts by weight of xylene and 10 parts by weight of poly(oxy-ethylene)-dodecyl-phenol ether (emulsifier) are thoroughly admixed. Thus an emulsifiable concentrate having an active ingredient content of 20% is obtained which may be converted by diluting with water into ready-for-use spray.

EXAMPLE 16

Granules 15 parts by weight of the compound according to Example 10, 81.5 parts by weight of China clay and 3.5 parts by weight of a polyvinyl alcohol type binding agent are admixed, powdered thoroughly homogenized. The mixture is kneaded with water, granulated and dried. The granules thus obtained having an active ingredient content of 15% may be used in this form or can be admixed with soil.

EXAMPLE 17

Floatable granules 10 parts by weight of the compound according to Example 7 are applied onto 85 parts by weight of pumice (particle size 0.5-1 mm) and the active ingredient is allowed to penetrate into the carrier. Then 5 parts by weight of liquid paraffin are sprayed onto the pumice. Thus ready-for-use floatable granules having an active ingredient content of 10% are obtained.

EXAMPLE 18

Coated granules 20 parts by weight of the compound according to Example 4 are applied onto 64 parts by weight of quartz sand (particle size 0.5-1 mm) and onto the particles 6 parts by weight of a 10% aqueous polyvinyl alcohol solution are sprayed. The granules are admixed with 10 parts by weight of white carbon. Thus ready-for-use coated granules having an active ingredient content of 20% are obtained.

EXAMPLE 19

Granules 10 parts by weight of the compound according to Example 9, 30 parts by weight of bentonite, 1 part by weight of calcium lignosulfonate, 0.1 part by weight of sodium lauryl sulfate and 58.9 parts by weight of China clay are homogenized. The mixture is kneaded with water, granulated by passing through a sieve having a suitable mesh-size and the granules are dried. Thus granules having an active ingredient content of 10% are obtained which may be used either in granular form or as a diluted aqueous solution.

What we claim is:

1. A phenanthrene derivative of the formula I

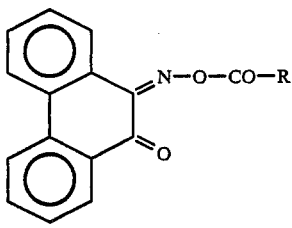 (I)

wherein,
R stands for $C_{1-10}$ alkylamino; $C_{1-10}$ alkylthio; $C_{1-5}$ alkoxy; unsubstituted phenylamino; or phenyl or phenylamino substituted on the phenyl ring by one or more identical or different $C_{1-4}$ alkyl, $C_{1-4}$ alkoxy, nitro, amino, cyano and/or halogen substituent(s).

2. A phenanthrene derivative as set forth in claim 1, wherein R stands for $C_{1-10}$ alkylamino or phenylamino optionally bearing on the phenyl ring one or more identical or different $C_{1-4}$ alkyl, $C_{1-4}$ alkoxy, nitro, amino, cyano and/or halogen substituent(s).

3. A phenanthrene derivative as set forth in claim 1, wherein R stands for $C_{1-5}$ alkoxy or $C_{1-10}$ alkylthio.

4. A phenanthrene derivative as set forth in claim 1, wherein R stands for phenyl substituted by one or more identical or different $C_{1-4}$ alkyl, $C_{1-4}$ alkoxy, nitro, cyano, amino and/or halogen substituent(s).

5. A phenanthrene derivative as set forth in claim 1, wherein R stands for $C_{1-5}$ alkylamino.

6. A phenanthrene derivative as set forth in claim 1, wherein R stands for $C_{1-10}$ alkylthio.

7. 9,10-phenanthrene-dione-9-(methylaminocarbonyl)-oxime.

8. 9,10-phenanthrene-dione-9-(n-butylaminocarbonyl)-oxime.

9. A composition for use in combatting harmful fungi in plants which comprises: a fungicidally effective amount of a compound of the formula I

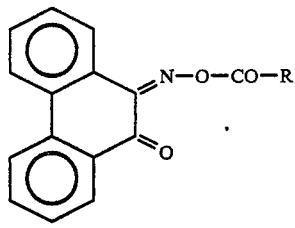 (I)

wherein,
R stands for $C_{1-10}$ alkylamino; $C_{1-10}$ alkylthio; $C_{1-5}$ alkoxy; or phenyl or phenylamino, the two latter groups being optionally substituted on the phenyl ring by one or more identical or different $C_{1-4}$ alkyl, $C_{1-4}$ alkoxy, nitro, amino, cyano and/or halogen substituent(s) combined with a diluent or solvent which is suitable for use in applying the composition to the plants.

10. A fungicidal composition according to claim 9, wherein the active ingredient is 9,10-phenanthrene-dione-9-(methylaminocarbonyl)-oxime or 9,10-phenanthrene-dione-9-(n-butylaminocarbonyl)-oxime.

11. A method for combating fungi in agriculture and horticulture, which comprises applying onto the plants, parts of plants, soil, the objects to be protected or onto the pests an effective amount of a composition according to claim 9.

12. A method for combating fungi as set forth in claim 11, wherein the active compound is 9,10-phenanthrene-dione-9-(methylaminocarbonyl)-oxime or 9,10-phenanthrene-dione-9-(n-butylaminocarbonyl)-oxime.

* * * * *